United States Patent [19]

Rüegg

[11] Patent Number: 4,465,473
[45] Date of Patent: Aug. 14, 1984

[54] INJECTION APPARATUS FOR THE DOSED DELIVERY OF A LIQUID

[75] Inventor: André Rüegg, Zürich, Switzerland

[73] Assignee: Contraves AG, Zürich, Switzerland

[21] Appl. No.: 438,456

[22] Filed: Nov. 1, 1982

[30] Foreign Application Priority Data

Nov. 24, 1981 [CH] Switzerland ............ 7500/81

[51] Int. Cl.³ ............................. A61M 5/20
[52] U.S. Cl. ..................................... 604/154
[58] Field of Search ............... 604/154, 155, 156, 151, 604/131, 207, 208, 186

[56] References Cited

U.S. PATENT DOCUMENTS

| | | | |
|---|---|---|---|
| 2,764,980 | 10/1956 | Smith | 604/154 |
| 3,504,777 | 4/1970 | Waugh | 192/136 |
| 3,701,345 | 10/1972 | Heilman et al. | 604/155 |
| 3,812,843 | 5/1974 | Wootten et al. | 604/155 |
| 4,157,716 | 6/1979 | Ruegg | 604/154 |
| 4,196,730 | 4/1980 | Wilson | 604/155 |
| 4,269,185 | 5/1981 | Whitney et al. | 604/155 X |

FOREIGN PATENT DOCUMENTS 2171971 9/1973 France .
1165842 10/1969 United Kingdom .

Primary Examiner—John D. Yasko
Attorney, Agent, or Firm—Werner W. Kleeman

[57] ABSTRACT

An injection apparatus for injecting liquids into a blood vessel of a living body includes an injector housing provided at its front end with a retaining or holder member for supporting an injection syringe containing a piston located in a cylinder of the injection syringe. The retaining member is adapted to exchangeably receive injection syringes of different cylinder cross-sections. A sensing device substantially comprises two sensing or feeler brackets and two switches cooperating with the sensing brackets. The sensing or feeler brackets are journaled in the retaining or holder member and are adapted to be deflected by interaction with the syringe cylinder. The deflection is particularly accomplished by a flange provided at one end of the syringe cylinder and having a diameter governed by the cylinder cross-section. Upon its deflection the sensing bracket actuates a related one of the switches to thereby transmit a signal dependent upon the cylinder cross-section to a control of a suitable drive arrangement containing a spindle mechanism in order to advance the piston at a controlled rate.

5 Claims, 5 Drawing Figures

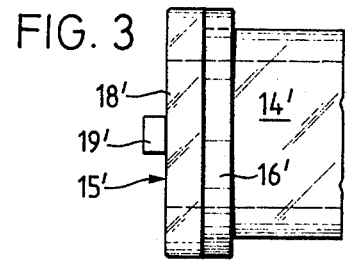
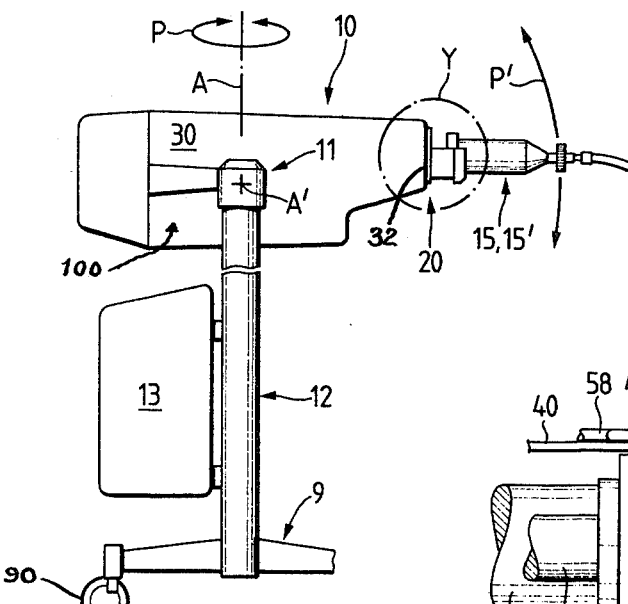
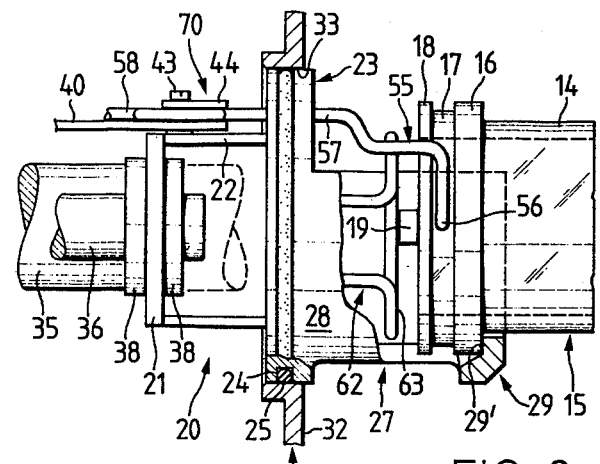
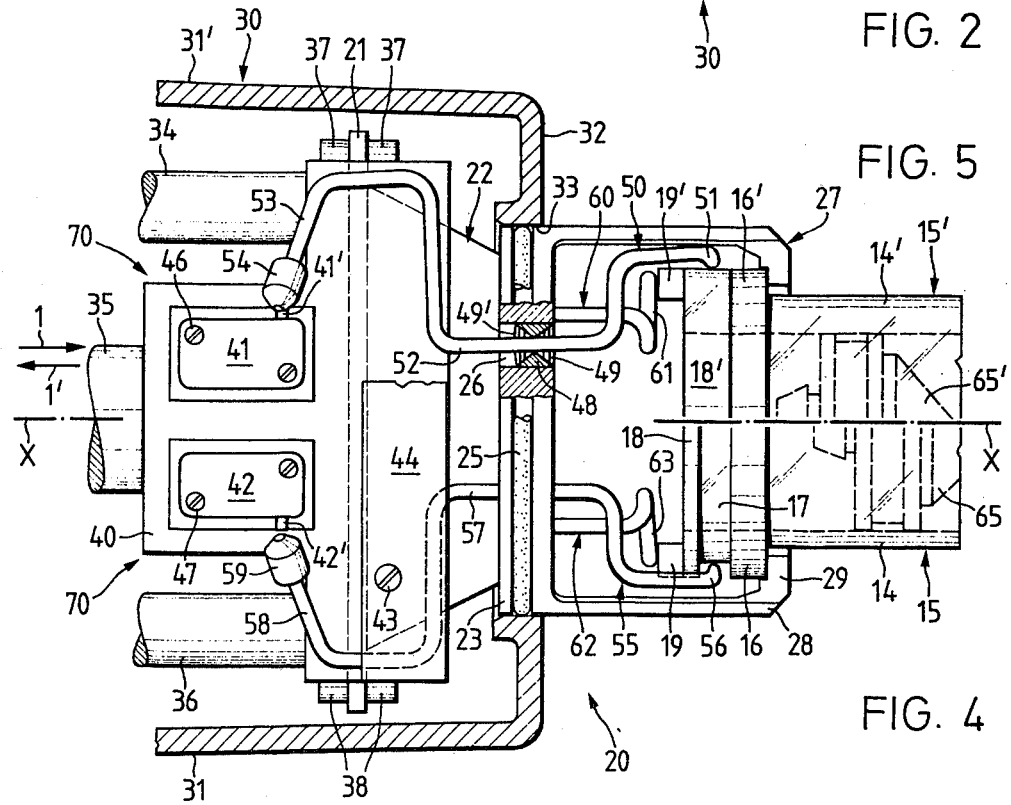

INJECTION APPARATUS FOR THE DOSED DELIVERY OF A LIQUID

CROSS-REFERENCE TO RELATED APPLICATION

This application is related to the commonly assigned, copending U.S. application Ser. No. 06/436,307, filed Oct. 25, 1982, entitled "Injection Syringe for the Successive Injection of Two Liquids into the Blood Vessels of Living Bodies".

BACKGROUND OF THE INVENTION

The present invention relates to a new and improved apparatus for the dosed delivery of a liquid to the blood vessel of a living being by using an injection syringe—sometimes briefly referred to as simply a syringe—, in particular to an injection apparatus of this type designed to be equipped with different injection syringes.

In its more particular aspects the injection apparatus of the present development is of the type comprising an injector housing which is provided with a drive arrangement containing a motor-driven spindle mechanism, and a retaining or holder member at the front end of the injector housing exchangeably receiving an injection syringe, the piston member of which is operatively connected to the aforementioned spindle mechanism and is displaceable within a cylinder of the syringe.

A device for the dosed delivery of a liquid is known from German Pat. No. 2,805,513 which substantially comprises an injector housing, a motor-driven spindle mechanism disposed in the injector housing, an injector syringe inserted into a retaining or holder member, and a piston member guided within a cylinder member of the injection syringe, said piston member being connected to a shaft of said spindle mechanism by means of a piston rod. A first scale drum is connected to the spindle shaft and a second scale drum is releasably coupled to the first scale drum, the scale drums being designed to limit the volume setting or adjustment and the advancing movement, respectively. By means of this prior art device a precise control, and thus, an injection corresponding exactly to the volume adjusted by the physician is ensured, which is vital for the life of the patient.

SUMMARY OF THE INVENTION

Therefore, with the foregoing in mind it is a primary object of the present invention to provide an improved construction of an injection apparatus for the dosed delivery of a liquid which is designed to be operated at the same degree of precision independent of the kind of syringe inserted into the retaining or holder member.

Another and more specific object of the present invention aims at the provision of a new and improved injection apparatus of the aforementioned type which readily responds to and is adapted to syringes having different cylinder diameters.

Still a further significant object of the present invention is directed to a new and improved construction of an injection apparatus for the dosed delivery of a liquid in which the rate of advancement or feed of the piston within the cylinder of the injection syringe is adjusted in dependence upon the cylinder cross-section of the injection syringe inserted into a retaining or holder member.

Another significant object of the present invention is directed to a new and improved construction of an injection apparatus for the dosed delivery of a liquid which is relatively simple in construction and design, quite economical to manufacture, extremely easy to use, not readily subject to breakdown or malfunction and which provides for the high degree of precision required in such type of apparatus.

Now in order to implement these and still further objects of the invention, which will become more readily apparent as the description proceeds, the injection apparatus of the present development is manifested by the features that, there is provided a flange member at a first end of the syringe cylinder and that at least one sensing or feeler bracket is journaled in the retaining or holder member and is adapted to be deflected, said sensing bracket having a sensor member at one end thereof which contacts the aforementioned flange and having an actuator member at the other end thereof. At least one switch is operatively associated with the actuator member of the sensing or feeler bracket, and the sensing bracket in the deflected position thereof actuates the associated switch. Consequently, a signal dependent upon the cross-section of the cylinder is transmitted to the spindle mechanism of the drive arrangement to correspondingly adjust the advancing rate of the piston in the syringe cylinder which is operatively connected to the spindle mechanism.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 1 is a front view of the injection apparatus according to the invention and shown mounted at a mobile stand arrangement;

FIG. 2 shows, partly in section, on an enlarged scale, details of the structure contained within the encircled portion of the injection apparatus marked by reference character Y in FIG. 1;

FIG. 3 is a front view of part of a second injection syringe intended to be inserted into the injection apparatus shown in FIG. 1;

FIG. 4 illustrates partly in section and partly in plan view one half of the retaining or holder member of the injection apparatus shown in FIG. 1 including the injection syringe depicted in FIG. 2; and FIG. 5 illustrates partly in section and partly in plan view one half of the retaining or holder member of the injection apparatus shown in FIG. 1 including the injection syringe depicted in FIG. 3.

DETAILED DESCRIPTION OF THE PREFERRED EMBODIMENTS

Describing now the drawings it is to be understood that in order to simplify the illustration only enough of the construction of the injection apparatus has been shown as needed for those skilled in the art to readily understand the underlying principles and concepts of the invention. Turning now specifically to FIG. 1 there has been illustrated schematically therein an exemplary embodiment of injection apparatus or device 10 which will be seen to essentially comprise a pedestal or base 9 mounted upon rollers 90, of which only one is particularly represented in the drawing, a post or upright 12, a swivel head 11 mounted to the top end of the post 12, and an injector housing 30 mounted by any suitable means at the swivel head 11. A control and operating console 13 is mounted laterally to the post or upright 12. The console 13 is operatively connected by connecting lines or conductors to a suitable drive arrangement, generally indicated by reference character 100, which contains a suitable motor-driven spindle mechanism which is disposed in the injector housing 30. The motor-driven spindle mechanism of the drive arrangement 100 may be, for instance, of the type disclosed in the commonly assigned U.S. Pat. No. 4,157,716, granted June 12, 1979. A further possible spindle drive arrangement is shown in the commonly assigned U.S. Pat. No. 3,523,523, granted Aug. 11, 1970.

As shown in FIG. 1, the injector housing 30 may be rotated about a vertical axis A in the direction of the double-headed arrow P, on the one hand, and may be appropriately pivoted about a horizontal axis A' in the direction of the double-headed arrow P', on the other hand, by means of the swivel head 11 mounted to the post or upright 11. A retaining or holder member 20 is arranged at a front end or wall 32 of the injector housing 30 and injection syringes 15 (FIG. 2) or 15' (FIG. 3) may be exchangeably inserted into the retaining or holder member 20.

With reference specifically to FIG. 2 there is shown, partly in section, details of the structure within the encircled portion marked by reference character Y in FIG. 1. The retaining or holder member 20, the syringe 15 and part of the syringe cylinder 14 of the syringe 15 will be immediately recognized in FIG. 2. This cylinder 14 is provided at one of its ends with a flange 18 followed in axial direction by an annular or ring-shaped groove 17 and a metal ring 16. The end face of the cylinder flange 18 is provided with at least two clamping cams or detents 19 spaced from each other.

The retaining or holder member 20 is fastened into the injector housing 30 by means of two supporting elements 34, 36 operatively connected to a mounting flange 21, as best seen by referring also to FIG. 5. The flange or flange member 23 is sealingly placed into the aperture 33 by means of a seal 25 located in an annular or ring-shaped groove 24. The supporting elements 34, 36 extend through the mounting flange 21 and are operatively connected to the retaining or holder member 20 by means of clamping elements 37, 38 of conventional design which are thus here not shown in greater detail.

The retainer element 27 formed integrally with the flange member 23 comprises, as shown in FIG. 2, a wall 28 which substantially forms a half-shell and an abutment or contact member 29 extending substantially parallel to the flange member 23. The abutment 29 includes an interior side or inner surface 29' which is designed to center the related injection syringe, such as the syringe 15 shown in FIG. 2.

Two spring or resilient elements 60, 62 formed, for instance, of spring wire are placed symmetrically in a mirror image relationship intermediate the interior side or inner surface 29' of the abutment 29 and the flange member 23. The spring element 60 is formed integrally with a part 61 which is resilient in axial direction on the side thereof facing the clamping cam or detent 19; the spring element 62 comprises a corresponding part 63.

The injection syringe can be inserted into the half-shell forming the retainer element 27. Due to the reaction force generated by the resilient parts 61, 63 the injection syringe will be urged against the interior side or inner surface 29' of the abutment or contact member 29.

A sensing or feeler device 70 comprising a first sensing or feeler bracket 55 will be furthermore recognized in FIG. 2. The first sensing bracket 55 essentially comprises a sensor member 56, a tilting or pivotal section 57 and an actuator member 58. A second sensing bracket 50 of the sensing device 70 cannot be recognized in FIG. 2 but a comparable arrangement is shown in FIG. 5; it is arranged and designed in mirror image relationship to the first sensing bracket 55. The second sensing bracket comprises a sensor member 51, a tilting or pivotal section 52 and an actuator member 53. In the arrangement of FIG. 2, both the bent-off sensor members 51 and 56 extend in circumferential or radial direction, for instance at least up to the center or central plane of the cylinder 14 or 14', respectively, when the respective injection syringe 15 or 15' is inserted into the retaining member 20. Both the tilting or pivotal sections 52 and 57 piercingly extend through the flange member 23; they are sealingly journaled in the flange member 23 and are adapted to be tilted or pivoted therein. Both the actuator members 53 and 58 engage or bear upon a support plate 40; they are retained substantially by means of a rail member 44 mounted to the support plate 40 by means of thread bolts or screws 43 or equivalent fastening expedients.

FIG. 3 shows part of the injection syringe 15'. The syringe cylinder 14' comprises a flange 18' located at the front region thereof, at the end face of which two clamping cams or detents 19' or the like are arranged near the circumference in diametrically opposed relationship. In axial direction a ring or ring member 16' follows the flange or flange member 18'.

To differentiate between the different cylinder cross-sections of the injection syringe 15 as shown in FIG. 2 and the injection syringe 15' as shown in FIG. 3, the flange 18 at the syringe cylinder 14 is provided with the annular or ring-shaped groove 17.

In FIGS. 4 and 5 there are shown one half each of the two different injection syringes 15 and 15' and the corresponding configurations of the injection apparatus. There will be recognized the injector housing 30 illustrated in section, the side walls 31 and 31' and the end wall 32 of the injector housing 30 as well as the retaining or holder member 20 retained by means of the flange or flange member 23 within the aperture 33. One half of the apparatus below the axis marked X—X is shown in FIG. 4 in combination with the inserted injection syringe 15 as shown in FIG. 2, while the other half depicted in FIG. 5 is shown with the inserted injection syringe 15' as shown in FIG. 3. The retaining member 20 is retained by the flange 23 which is sealingly held in the aperture or opening 33, on the one hand, and by the supporting elements 34, 36 which are arranged symmetrically with respect to the axis X—X, on the other hand. The supporting elements 34 and 36 are appropriately secured by means of the clamping elements 37 and 38, respectively, to the mounting flange 21 of the retaining member 20. Furthermore, FIGS. 2, 4 and 5 show part of a plunger 35 passing by means of one end thereof through the retaining or holder member 20, and this plunger 35 is operatively connected in any suitable manner with the piston member 65 or 65' in the cylinder 14 or 14', respectively, of the related injection syringe 15 or 15', respectively. At the other end the plunger 35 is operatively connected to the spindle mechanism of the multi-speed drive arrangement 100 located in the injector housing 30. Hence, the plunger 35 and thus the related piston member 65 or 65', respectively, may be advanced in the direction of the arrow 1 for injection and in the direction of arrow 1' after conclusion of the injection.

The sensing or feeler device 70 is illustrated on an enlarged scale and in plan view in FIGS. 4 and 5. This sensing device 70 essentially comprises the sensing or feeler brackets 50, 55 arranged symmetrically in a mirror image relationship with respect to the axis X—X and passing through the flange 23 of the retaining member 20, as well as two switches 41 and 42 or equivalent structure mounted to the supporting plate 40 by means of the threaded bolts or screws 46 and 47, respectively.

The first sensing or feeler bracket 55 formed in one piece from spring wire has a sensor member 56 at one end and an actuator member 58 at the other opposed end, both said members being interconnected substantially by the tilting or pivotal section 57. A contact or contacting element 59 is mounted at the end of the actuator member 58 and is operatively associated with a push button 42' or the like of the switch 42; it is fastened to the end of the actuator member 58 by any suitable means. The second sensing bracket 50 is designed analogously to the first sensing or feeler bracket 55 and comprises the sensor member 51, the actuator member 53 as well as the intermediate tilting or pivotal section 52 interconnecting the members 51 and 53. At the end of the actuator member 53 there is likewise provided a contact or contacting element 54 which is operatively associated with the push button 41' of the switch 41.

FIG. 5 shows, partly in section, the manner in which the second sensing bracket 50 is pivotably journaled in the flange or flange member 23 of the retaining member 20. A bore 26 passing through the flange 23 will be recognized and the tilting or pivotal section 52 is movably journaled in a bearing member 48 provided with centering means forming conical rings. Sealing elements 49, 49' are disposed on both sides of the bearing member 48. Each one of the sealing elements 49, 49' is secured to the related inclined face of the bearing member 48, on the one side, and to the circumferential face of the tilting or pivotal section 52, on the other side, by means of an adhesive or by a vulcanized connection, by way of example.

The tilting or pivotal section 57 of the first sensing bracket 55 is journaled in the flange member 23 of the retaining member 20 analogously to the journaling of the tilting section 52 as described hereinbefore.

In the description to follow there will be now explained in detail the use of the inventive injection apparatus in conjunction with, strictly by way of example and not limitation, the use of two injection syringes, such as the syringes 15 and 15', having different diameters of their related syringe cylinders. As a matter of introduction reference is made thereto that the sensing brackets 50 and 55 journaled in the flange 23 of the retaining member 20 are arranged symmetrically in a mutual mirror image relationship in the absence of an inserted injection syringe and are retained in a neutral position where they do not actuatingly contact the switches 41 and 42. Furthermore, both the sensor members 51 and 56, on the one hand, and both the actuator members 53 and 58, on the other hand, are spaced apart at the same distance as seen from the axis X—X. In the embodiment as shown, the distance between the two sensor members 51 and 56 corresponds to the diameter of the annular or ring-shaped groove 17 provided for the flange or flange member 18 of the injection syringe 15.

According to the embodiment illustrated in FIG. 4, the injection syringe 15 is inserted into the retaining or holder member 20 such that the clamping cam or detent 19 and the part 63 of the spring element 62 are in solid engagement and the ring member 16 of the injection syringe 15 is urged against the interior side 29' of the abutment 29. In such an arrangement the sensor member 56 of the first sensing bracket 55 is located within the annular groove 17 and the contacting element 59 at the actuator member 58 is spaced from the push button 42' of the related switch 42. In such a position the switch 42 is not actuated and the injection then occurs by displacement of the piston member 65 within the cylinder 14 of the injection syringe 15 at a first rate of advancement in correspondence with the direction of arrow 1, said rate of advancement being determined by the cross-section of the cylinder 14 in injection syringe 15.

In the exemplary embodiment as shown in FIG. 5, the part 61 of the spring element 60 is in solid engagement with the clamping cam or detent 19' of the injection syringe 5' which is inserted into the retaining member 20. The ring member 16' of the injection syringe 15' is urged against the interior side or inner surface of the abutment 29. In this arrangement the sensor member 51 solidly engages or snugly bears against the outer periphery of the flange or flange member 18'. The flange 18' is of different, greater diameter than the annular groove 17 provided at the circumference of the flange 18 of the injection syringe 15. Therefore, the sensing bracket 50 journaled in the flange 23 will become deflected due to the change in the radial distance. Due to the deflection the sensor member 51 will move radially outwardly, while the actuator member 53 will move radially inwardly. Consequently, the contacting element 54 at the actuator member 53 will actuate the push button 41' of the related switch 41. Due to the actuation of switch 41 an electronic circuit within the controlling and operating console 13 is activated to transmit a signal which corresponds to the cross-section of the injection syringe 15' to the spindle mechanism of the drive arrangement 100. In this way, the plunger-piston member combination 35, 65' will be advanced at a rate which is different from the rate in the former case in which the injection syringe 15 of a different cross-section had been inserted into the retaining member 20. The injection apparatus as described hereinbefore thus is able to positively control the rate of advancement of the piston member in the cylinder of injection syringes having different diameters in such a way that the rate of advancement or feed depends upon the cylinder cross-section or cross-sectional area.

The sensing device 70 as described hereinbefore in combination with the associated switches 41, 42 or the like is particularly suited to respond to different cylinder cross-sections of two different injection syringes. Hence, the flange 18 of one injection syringe is provided, for instance, with an annular groove 17 as a reference to the diameter of the syringe cylinder 14 (cf. FIG. 4). The flange 18' of the other injection syringe is related to the cylinder cross-section of the syringe cylinder 14'; the diameter of the flange 18' is larger as compared to that of the flange 18 (cf. FIG. 5). However, the flange 18' may also be provided instead with an annular or ring-shaped groove having a greater diameter than the annular groove 17 in the flange 18 of the other injection syringe.

Additionally, there is the possibility of using stepping switches of corresponding design in association with both the actuator members 53 and 58 in the sensing or feeler device 70. In such a case various injection syringes may be inserted into the retaining member 20 and the different injection syringes will have flanges with different diameters related to the respective cylinder cross-section of a respective injection syringe. Again the control of the rate of advancement or feed of the plunger-piston member combination will be affected depending on the cylinder cross-section by means of the electronic circuit as mentioned before by means of which a corresponding signal is transmitted to the spindle mechanism of the drive arrangement.

While there are shown and described present preferred embodiments of the invention, it is to be distinctly understood that the invention is not limited thereto, but may be otherwise variously embodied and practiced within the scope of the following claims. Accordingly,

What I claim is:

1. An injection apparatus for the dosed delivery of a liquid comprising:
   an injector housing having a front end;
   a retaining member arranged at said front end of said injector housing;
   said retaining member being adapted to exchangeably retain therein injection syringes;
   each said injection syringe comprising a hollow cylinder having a first end, a second end and a defined cross-section and including a piston member guided for displacement therein intermediate said first and said second ends;
   said first end of said hollow cylinder being provided with a flange member;
   at least one sensing bracket journaled in said retaining member such as to enable deflections of said sensing bracket;
   said sensing bracket having a sensor member at one end thereof for contacting said flange member at said first end of said hollow cylinder and having an actuator member at the other end thereof; and
   at least one switch operatively associated with said actuator member of said at least one sensing bracket;
   whereby said sensing bracket in a deflected position thereof actuates said switch which is capable of transmitting a signal dependent on the cross-section of said cylinder for controlling the rate of advancement of said piston member of said injection syringe.

2. The injection apparatus as defined in claim 1, wherein:
   a flange is provided in the retaining member;
   two of said sensing brackets are journaled in said flange of said retaining member in a substantially mirror image relationship symmetrically with respect to each other; and
   means for pivotably and sealingly journaling a pivotal section of each of said sensing brackets in said flange such as to enable each said sensing bracket to tiltably move.

3. The injection apparatus as defined in claim 1, wherein:
   the flange member at the first end of the hollow cylinder has an outer diameter governed by the cross-section of said hollow cylinder in order to be able to differentiate between different ones of said injection syringes.

4. The injection apparatus as defined in claim 3, wherein:
   the flange member at the first end of the hollow cylinder has an annular groove in a peripheral face thereof;
   said annular groove having an outer diameter governed by the cross-section of said hollow cylinder;
   the sensor member of the sensing bracket engaging with said annular groove; and
   said sensor member extending in circumferential direction of said annular groove at least up to the region of a plane containing a center line of the hollow cylinder of the injection syringe inserted into the retaining member.

5. An injection apparatus for the dosed delivery of a liquid comprising:
   an injector housing;
   syringe retaining means supported by said injector housing;
   said syringe retaining means being structured to exchangeably retain therein different injection syringes;
   each said injection syringe comprising a hollow cylinder having a first end, a second end and a defined cross-section and including a piston member guided for displacement therein intermediate said first and said second ends;
   said first end of said hollow cylinder being provided with means characteristic of the size of such injection syringe;
   at least one displaceable sensing bracket operatively associated with said syringe retaining means;
   said sensing bracket having a sensor member at one end region thereof intended to cooperate with said characteristic means at said first end of said hollow cylinder and having an actuator member at another end region thereof; and
   at least one switch operatively associated with said actuator member of said at least one sensing bracket,
   whereby said displaceable sensing bracket in response to displacement movements thereof assumes a predetermined position with respect to said switch to control in a predetermined manner the rate of advancement of said piston member of said injection syringe.

* * * * *